(12) United States Patent
Redford et al.

(10) Patent No.: US 10,344,309 B2
(45) Date of Patent: Jul. 9, 2019

(54) METHODS OF COMPRESSING LIGNOCELLULOSIC FEEDSTOCK INTO DISCRETE UNITS, AND RELATED SYSTEMS

(71) Applicant: POET Research, Inc., Sioux Falls, SD (US)

(72) Inventors: Steven G. Redford, Brandon, SD (US); Todd L. Peterson, Brandon, SD (US)

(73) Assignee: POET Research, Inc., Sioux Falls, SD (US)

( * ) Notice: Subject to any disclaimer, the term of this patent is extended or adjusted under 35 U.S.C. 154(b) by 547 days.

(21) Appl. No.: 15/085,206

(22) Filed: Mar. 30, 2016

(65) Prior Publication Data

US 2016/0289720 A1  Oct. 6, 2016

Related U.S. Application Data (60) Provisional application No. 62/142,773, filed on Apr. 3, 2015.

(51) Int. Cl.

| | | |
|---|---|---|
| *C12P 19/02* | (2006.01) | |
| *C12P 19/14* | (2006.01) | |
| *C12M 1/00* | (2006.01) | |
| *C12M 1/33* | (2006.01) | |
| *C12M 1/40* | (2006.01) | |
| *D21B 1/02* | (2006.01) | |
| *D21B 1/06* | (2006.01) | |

(52) U.S. Cl.
CPC ............ *C12P 19/14* (2013.01); *C12M 21/18* (2013.01); *C12M 39/00* (2013.01); *C12M 45/02* (2013.01); *C12P 19/02* (2013.01); *D21B 1/02* (2013.01); *D21B 1/023* (2013.01); *D21B 1/063* (2013.01); *C12P 2201/00* (2013.01)

(58) Field of Classification Search
CPC ....... C12P 19/02; C12P 19/14; C12P 2201/00; C12M 39/00; C12M 45/02; C12M 21/18; D21B 1/02; D21B 1/023; D21B 1/063
See application file for complete search history.

(56) References Cited

U.S. PATENT DOCUMENTS

| | | | |
|---|---|---|---|
| 5,352,252 A | 10/1994 | Tolmie | |
| 5,424,417 A | 6/1995 | Torget et al. | |
| 5,657,621 A | 8/1997 | Mendes et al. | |
| 6,022,419 A | 2/2000 | Torget et al. | |
| 6,855,182 B2 | 2/2005 | Sears | |
| 7,811,339 B2 | 10/2010 | Werner | |
| 8,318,064 B2 * | 11/2012 | Parish | C10L 5/44 264/140 |
| 8,450,094 B1 | 5/2013 | Narendranath et al. | |
| 8,551,549 B2 * | 10/2013 | Zeeck | C10L 5/44 426/442 |
| 8,753,410 B2 | 6/2014 | Taulbee | |
| 8,852,301 B1 | 10/2014 | Bootsma | |
| 2010/0196981 A1 | 8/2010 | Aharon et al. | |
| 2010/0233771 A1 | 9/2010 | McDonald et al. | |
| 2011/0111456 A1 | 5/2011 | Medoff | |
| 2013/0143290 A1 | 6/2013 | Narendranath | |

FOREIGN PATENT DOCUMENTS

WO    2006/102543 A2    9/2006

OTHER PUBLICATIONS

International Search Report and Written Opinion from International Application No. PCT/US2016/024946, dated Jun. 16, 2016 (11 pages).

* cited by examiner

*Primary Examiner* — David A Reifsnyder
(74) *Attorney, Agent, or Firm* — Kagan Binder, PLLC (57) ABSTRACT

The present disclosure relates to methods of processing lignocellulosic feedstock that include grinding lignocellulosic feedstock to provide ground lignocellulosic feedstock; and compressing at least a portion of the ground lignocellulosic feedstock to form at least one discrete unit. In some embodiments, a plurality of discrete units have a bulk density in the range from 4 pounds per cubic foot to 25 pounds per cubic foot. The present disclosure also includes related systems.

20 Claims, 5 Drawing Sheets

METHODS OF COMPRESSING LIGNOCELLULOSIC FEEDSTOCK INTO DISCRETE UNITS, AND RELATED SYSTEMS

RELATED APPLICATION

The present non-provisional Application claims the benefit of commonly owned provisional Application having Ser. No. 62/142,773, filed on Apr. 3, 2015, which provisional Application is incorporated herein by reference in its entirety.

FIELD

The present disclosure is related to methods and/or systems for processing lignocellulosic feedstock to form at least one discrete unit. More particularly, the present disclosure is related to methods and/or systems for compressing ground lignocellulosic feedstock to form a plurality of discrete units having a desirable bulk density.

BACKGROUND

Lignocellulosic feedstock can be used to make one or more biochemicals (e.g., ethanol) in a biorefinery. For example, lignocellulosic feedstock can include one or more polysaccharide molecules (e.g., hemicellulose and/or cellulose) that can be broken down using a variety of techniques to create monosaccharides. The monosaccharides can be used by a microorganism (e.g., yeast) to create one or more biochemicals via a biochemical conversion process such as fermentation. The biochemical(s) can be concentrated by a variety of techniques such as distillation.

Handling and/or processing lignocellulosic feedstock in a biorefinery to form monosaccharides and/or a biochemical such as ethanol can involve one or more challenges due to, e.g., the size and/or bulk density of the lignocellulosic feedstock. For example, lignocellulosic feedstock such as agricultural residue (e.g., corn stover) can be ground to facilitate processing it to produce one or more biochemicals. In some instances, corn stover can be harvested, baled, and transported to a facility that produces biochemicals. The bales of corn stover can be unbaled at the biorefinery and ground to an average size of 10 inches or less, or even 4 inches or less. The ground corn stover can be transported within the biorefinery via a conveying system. If the ground corn stover is being transferred through an opening, the ground corn stover can bridge across the opening and pile up to an undue degree. In some embodiments, the ground corn stover can pile up in a manner so as to prevent flow of the ground corn stover through the opening which can damage equipment in the conveying system. Because of the bulk density of the ground stover, such conveying systems can be relatively large and occupy a substantial amount of space within a biorefinery.

Another example of a challenge related to processing lignocellulosic feedstock involves processing lignocellulosic feedstock in an apparatus that separates liquids from solids. For example, lignocellulosic feedstock such as corn stover can be ground and mixed with a liquid aqueous composition such as water to form a slurry and treat the ground corn stover. The ground corn stover in the slurry can be treated to break down polysaccharides (e.g., hemicellulose and/or cellulose) into oligosaccharides and/or monosaccharides (e.g., pentose and/or hexose). After treating the ground corn stover in the slurry, at least a portion of the remaining solids from the ground corn stover can be separated from at least a portion of the liquid in the slurry. In some instances, a screen can be used to separate the remaining solids from the liquid. The remaining ground corn stover solids can be relatively straight fibrous material that can plug the screen to an undue degree. In some embodiments, the remaining corn stover solids can build up to a degree that substantially prevents liquid from passing through the screen.

SUMMARY

Disclosed in embodiments herein are methods of processing lignocellulosic feedstock that include grinding lignocellulosic feedstock to provide ground lignocellulosic feedstock; and compressing at least a portion of the ground lignocellulosic feedstock to form a plurality of discrete units, wherein the plurality of discrete units have a bulk density in the range from 4 pounds per cubic foot to 25 pounds per cubic foot as measured by ASAE S269.4.

Further disclosed in embodiments herein are systems for processing lignocellulosic feedstock that include a source of lignocellulosic feedstock; a grinding system configured to grind the lignocellulosic feedstock to provide ground lignocellulosic feedstock, and a compressing system configured to compress at least a portion of the ground lignocellulosic feedstock to form a plurality of discrete units, wherein the plurality of discrete units have a bulk density in the range from 4 pounds per cubic foot to 25 pounds per cubic foot as measured by ASAE S269.4, wherein the grinding system is in fluid communication with the compressing system.

DETAILED DESCRIPTION

Disclosed in embodiments herein are methods and/or systems of processing lignocellulosic feedstock to form discrete units.

Lignocellulosic Feedstock

Lignocellulosic feedstock can include lignin, hemicellulose, and cellulose. In the context of a biochemical conversion process such as making a biochemical (e.g., ethanol)

using a microorganism, a lignocellulosic feedstock can be treated to generate sugars via hydrolysis. In exemplary embodiments, a lignocellulosic feedstock can include corn stover (leaves and stalks and cobs), alfalfa, grasses, soybean stubble, hogged wood, switch grass, miscanthus, straw, sawdust, and the like.

As used herein, "feedstock" refers to lignocellulosic material that is minimally processed, if at all, prior to grinding and compressing. For example, lignocellulosic feedstock can refer to lignocellulosic material that is in a "green state," which means the feedstock has been recently harvested from a farm or plantation where it was grown. As another example, lignocellulosic feedstock can refer to lignocellulosic material that has been aged (e.g., either in a storage system or in the field where it was grown). Minimal processing that the lignocellulosic feedstock may experience prior to grinding and compressing includes unbaling, cleaning (e.g., to remove dirt and other foreign material), wetting (e.g., to control moisture), drying (e.g., to control moisture), combinations of these, and the like. Further, a lignocellulosic feedstock means a lignocellulosic material that can be compressed to form a plurality of discrete units having a bulk density in the range from 4 pounds per cubic foot to 25 pounds per cubic foot.

A lignocellulosic feedstock can be made available as a source of lignocellulosic feedstock for grinding. For example, the lignocellulosic feedstock can be transported to a biorefinery in bales or as a loose material. A bale of lignocellulosic feedstock can include twine, netting, and the like that can wrap around the lignocellulosic feedstock and secure the lignocellulosic feedstock in the form of a bale (e.g., rectangular bale).

If the lignocellulosic feedstock is provided in the form of a bale, the bale can be unbaled prior to grinding. A bale of lignocellulosic feedstock can be manually unbaled or can be subjected to an unbaling device in an unbaling system to remove the twine or netting so that the lignocellulosic feedstock is loose enough such that it can be fed to a grinding system.

Grinding Lignocellulosic Feedstock

The lignocellulosic feedstock can be ground to provide ground lignocellulosic feedstock. Grinding the lignocellulosic feedstock can help provide the lignocellulosic feedstock in a size that is desirable for subsequent compression. For example, the lignocellulosic feedstock can be ground to a size based on the size of an extruder die for compressing the ground feedstock, and vice versa (discussed below).

Further, grinding can provide a relatively more uniform size of lignocellulosic feedstock, which can facilitate forming relatively uniform discrete units.

The lignocellulosic feedstock can be ground in a grinding system configured to grind the lignocellulosic feedstock to provide ground lignocellulosic feedstock. In some embodiments a grinding system can include one or more grinding devices such as forage choppers, hammer mills, tub grinders, knife mills, and the like, and combinations thereof. The particle size of the ground lignocellulosic feedstock can be controlled via one or more of screen size, rotor rpm, feed rate, etc.

Cleaning the Lignocellulosic Feedstock

Optionally, the lignocellulosic feedstock can be cleaned prior to compressing. Cleaning involves removing non-lignocellulosic feedstock material from the lignocellulosic feedstock. Exemplary non-lignocellulosic feedstock material includes dirt, silt, sand, rocks, tramp metal, glass, and the like.

In some embodiments, such cleaning occurs before compressing. In some embodiments, cleaning occurs after grinding and before compressing.

Cleaning lignocellulosic feedstock is further discussed below in connection with FIG. 3.

Compressing Ground Lignocellulosic Feedstock

Figure 1:
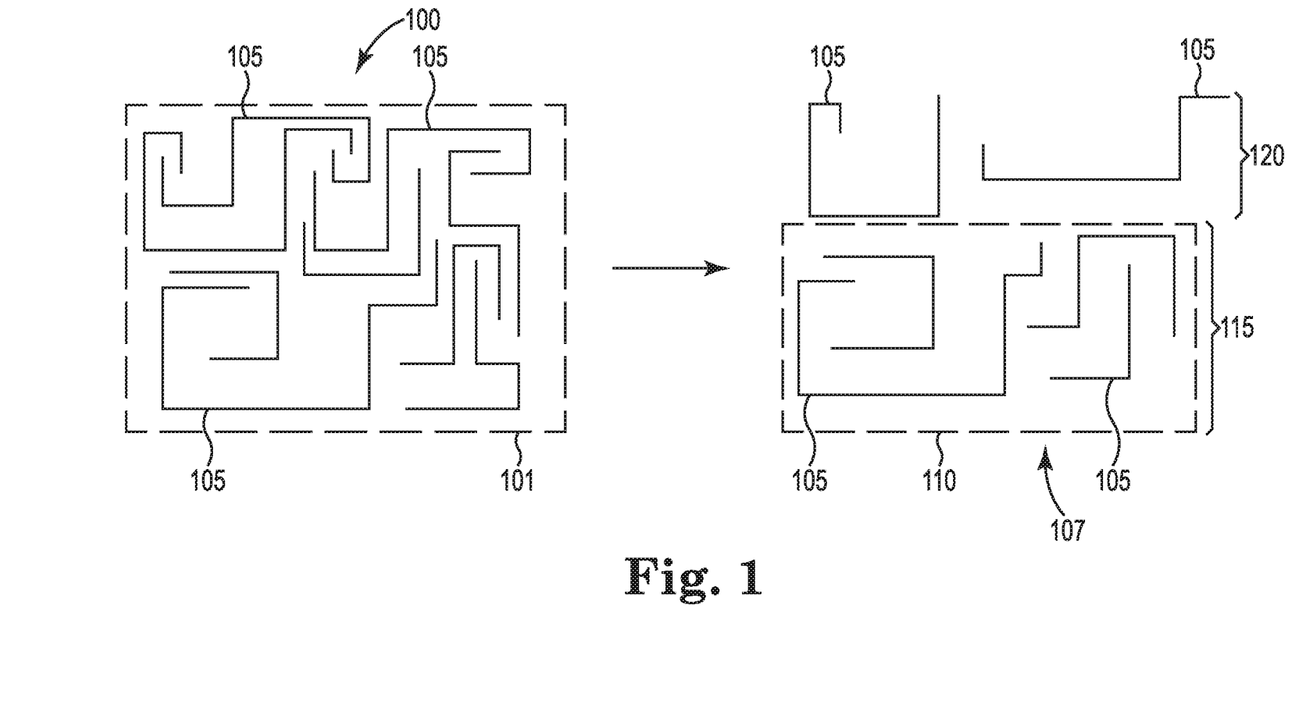
FIG. 1 schematically illustrates an embodiment of a discrete unit formed from lignocellulosic feedstock according to the present disclosure.

After grinding, at least a portion of the ground lignocellulosic feedstock can be compressed to form at least one discrete unit. While not being bound by theory, it is believed that a discrete unit of compressed ground lignocellulosic feedstock can include a plurality of individual pieces of ground lignocellulosic feedstock that are bent due to compression and in a manner so that the individual pieces form an interlocking structure to form the discrete unit. An example of discrete unit formed from lignocellulosic feedstock is schematically illustrated in FIG. 1. As shown in FIG. 1, discrete unit 100 includes individual pieces 105 of compressed, ground lignocellulosic feedstock that have a bent structure due to compression such that the pieces 105 interlock with each other. The dotted line 101 represents the generally rectangular shape of discrete unit 100. In some embodiments, it is believed that lignocellulosic feedstocks such as corn stover and those similar to corn stover can be particularly desirable because their natural form can be bent under compression and interlocked with other like pieces of compressed ground lignocellulosic feedstock, thereby forming a discrete unit.

Notably, in many embodiments chemical binders are not necessary to form a discrete unit. Also, mechanical binders such as twine, netting, and the like can be avoided. The interlocking structure described above can be sufficient to form a self-contained discrete unit that remains self-contained for at least a portion of a biochemical process such as producing ethanol from sugar.

In some embodiments, one or more chemical binders can be used to facilitate forming a discrete unit. Exemplary chemical binders include one or more of clay (e.g., bentonite), starch, gum, and the like, and combinations thereof. Suitable chemical binders are commercially available under the trade names Ameri-Bond 2X® and PellTech from Borregaard LignoTech, Sarpsborg, Norway.

Compressing the ground lignocellulosic feedstock can densify relative to the uncompressed ground lignocellulosic feedstock, but the compressed, ground lignocellulosic feedstock can have a relatively low enough density that corresponds to a three-dimensional structure that is sufficiently open so as to permit fluids to effectively penetrate and treat the compressed, ground lignocellulosic feedstock. For example, one or more liquid aqueous compositions (e.g., liquid aqueous compositions including acid, enzymes, and the like) can penetrate the compressed, ground lignocellulosic feedstock and contact a desired surface area of the compressed, ground lignocellulosic feedstock so as to help break down a desired amount of polysaccharides into monosaccharides in a desirable time period.

In some embodiments, at least a portion of the ground lignocellulosic feedstock can be compressed to form a plurality of discrete units, where the plurality of discrete units have a bulk density in the range from 4 pounds per cubic foot to 25 pounds per cubic foot. As used herein, "bulk density" means the mass (e.g., pounds) of a plurality of discrete units of compressed, ground lignocellulosic feedstock that fill a container of known volume (e.g., a cubic foot box) divided by the total weight (e.g., pounds) of the plurality of discrete units. The total weight of the plurality of discrete units of compressed, ground lignocellulosic feedstock can be obtained by weighing the container full of the plurality the discrete units and then subtracting the weight of the empty container. In some embodiments, the bulk density can be measured according to ASAE S269.4, which is incorporated herein by reference.

According to ASAE S269.4, a cylindrical container, 380 mm (15 in.) in diameter and 495 mm (19.5 in.) high (inside dimensions), shall be used. Divide the net mass, in kg, of the material by 0.05615 m3 (2.00 ft3) to obtain bulk density in kg/m3 (lb/ft3). The container shall be filled by pouring from a height of 610 mm (2 ft) above the top edge of the container. The container shall then be dropped 5 times from a height of 150 mm (6 in.) onto a hard surface to allow settling. In the case of small pellets and crumbles, the material shall be struck off level with the top surface. In the case of cubes and large pellets, remove the cubes or large pellets which have more than one half their volume above the top edge of the container, leaving in the container those cubes or large pellets with more than one half their volume below the top edge of the container. The density determined by this method shall be corrected to 0% moisture content by the use of the equation in paragraph 3.2.9 under Unit Density. Because of the tendency for cubes to expand for some time after forming, both the time interval between forming and this measurement, and the moisture content at the time of this measurement, should be specified when dealing with cubes. Bulk density measurements should be repeated at least 3 times and the average value reported.

In some embodiments, at least a portion of the ground lignocellulosic feedstock can be compressed to form a plurality of discrete units having a bulk density in the range from 8 pounds per cubic foot to 25 pounds per cubic foot. In some embodiments, at least a portion of the ground lignocellulosic feedstock can be compressed to form plurality of discrete units having a bulk density in the range from 13 pounds per cubic foot to 18 pounds per cubic foot.

Advantageously, the discrete units of compressed, ground lignocellulosic feedstock can have better flow character as compared to the uncompressed ground lignocellulosic feedstock. For example, the discrete units tend to pass through (e.g., drop through) an opening instead of bridging across an opening and building up to an undue degree. In some embodiments, relatively consistent and uniform discrete units can be formed, which helps the compressed, ground lignocellulosic feedstock be metered relatively more accurately as compared to the uncompressed ground lignocellulosic feedstock.

Also, the relatively more dense discrete units of compressed, ground lignocellulosic feedstock can be transported with a relatively smaller conveyor system to achieve a desired throughput as compared to the uncompressed ground lignocellulosic feedstock.

As yet another advantage, the discrete units of compressed, ground lignocellulosic feedstock (or a portion thereof) can have a reduced tendency to plug a screen used to separate at least a portion of a liquid from a solid. Without being bound by theory, it is believed that the bent structure of the compressed, ground lignocellulosic feedstock helps prevent the lignocellulosic feedstock from lying flat on the screen and building up to an undue degree such that liquid can barely pass, if at all, through the screen. Instead, the bent structure can permit liquid to pass through the screen at a desired flow rate even though the bent lignocellulosic feedstock may build up on a side of the screen.

As a discrete unit of compressed, ground lignocellulosic feedstock is handled and/or processed through a biorefinery (e.g., an ethanol production facility), one or more of the individual pieces may separate from the originally formed discrete unit. The individual pieces that may separate from the originally formed discrete unit tend to remain in bent form which can still facilitate improved handling and/or processing as compared to ground lignocellulosic feedstock that has not been compressed as described herein. For example, even though one or more individual pieces of ground lignocellulosic may separate from the originally formed discrete unit the bent structure can help prevent bridging as the individual pieces of ground lignocellulosic feedstock are conveyed through an opening and/or can help prevent the individual pieces from getting stuck in liquid/solid separation screen and plugging said screen. Liquid/solid separation devices that include screens are further discussed below in connection with separating system 245.

An example of how one or more of the individual pieces may separate from the originally formed discrete unit is schematically illustrated in FIG. 1. As shown in FIG. 1, one or more individual pieces of lignocellulosic feedstock 105 may separate from discrete unit 100. The separated pieces of lignocellulosic feedstock 105 are shown as 120. At least some individual pieces of lignocellulosic feedstock 105 may remain interlocked so as to form a smaller discrete unit 107 and is identified by 115. Dotted line 110 represents the general shape of discrete unit 107. As can be seen in FIG. 1, the separated pieces of lignocellulosic feedstock 105 and 120 tend to retain their bent structure from being subjected to compression. Such a bent structure can reduce the tendency of even the individual pieces 105 from plugging a screen design to separate solids and liquids as compared to pieces of lignocellulosic feedstock having a straight (unbent) shape.

A discrete unit of compressed, ground lignocellulosic feedstock can be characterized in terms of durability value reported as Pellet Durability Index, which is measured according to the methodology in ASAE S269.4, the entirety of which standard is incorporated herein by reference. According to ASAE S269.4, the durability (Pellet Durability Index) of cube form discrete units can be determined by tumbling a test sample for 3 min at 40 r/min. The outside dimensions of the angle iron frame of the tumbler are shown in FIG. 1 of ASAE S269.4. The covering shall be 12.5 mm (0.5 in.) mesh hardware cloth applied taut to the outside of the frame. Interior projections, such as screw heads, should be kept to a minimum and should be well rounded. The box shall be mounted on a diagonal axis (2 planes) with 2 stub shafts terminating at the exterior of the angle iron frame. These may be hollow shafts for ease of fabrication. There will be a hinged triangular door 300×300×430 mm (12×12×17 in.) on each end. The axis of rotation shall be horizontal (see FIG. 1 of ASAE S269.4). To determine durability of discrete units in the form of cubes, the cubes shall be tested by tumbling a representative 10 cube sample, whose individual mass does not vary over +/−10% of the average original mass, in the manner described in paragraph 5.1.1 of ASAE S269.4. Care should be taken that cubes are not broken or disintegrated after they have been weighed and during loading into the tumbler. After this tumbling test, the total mass of all particles each weighing more than 20% of the average initial cube mass shall be recorded and designated as cube size material, CSM. The durability rating for cubes is expressed as the percentage of CSM over 20% of the average initial cube mass. Using the original average cube mass, compute 5 mass classes, each expressing 20% increments of the original average cube mass. Separate the cube pieces remaining after tumbling into piles prescribed by the 5 mass classes. Pieces weighing more than the average original cube mass will be included in the highest mass class. The percentage of material in each class shall then be determined by dividing the total mass in each class by the total mass before testing. A size-distribution index of the durability is then obtained by multiplying the percentage of material in each of the 5 classes from highest to lowest, respectively, by four (4), three (3), two (2), one (1), zero (0), and then calculating the summation of products obtained by this method. A perfect index is 400 (see Table 1 of ASAE S269.4).

Alternatively, durability can be determined sample is sifted with a sieve, typically a US #7 (2819 micron) sieve to get a 500 gram sample with no fines. The sifted sample is then placed into a tumbling can and tumbled for a time period of about 5 minutes. The tumbled sample is then sifted on the #7 screen again to remove fines. The non-fine component is then weighed. That weight/500×100% gives a percentage that can be used to characterize durability.

In some embodiments, the discrete units have a Pellet Durability Index of less than 90 as measured by ASAE 5269.4. In some embodiments, the discrete units have a Pellet Durability Index of less than 50 as measured by ASAE 5269.4. In some embodiments, the discrete units have a Pellet Durability Index in the range of greater than 0 to 60 as measured by ASAE 5269.4. In some embodiments, the discrete units have a Pellet Durability Index in the range of 5 to 50 as measured by ASAE 5269.4.

A discrete unit of compressed, ground lignocellulosic feedstock can have any desired shape. The shape can be determined at least in part based on how the discrete unit was formed (e.g., the shape of an extruder die used to compressed the feedstock). In some embodiments, the discrete units of compressed, ground lignocellulosic feedstock can be in the shape of a rectangular prism, cylindrical, hexagonal, cube, etc.

A discrete unit of compressed, ground lignocellulosic feedstock can have any desired size. The size can be determined at least in part based on how the discrete units were formed (e.g., the size of an extruder die used to compressed the feedstock). In some embodiments, the discrete units of compressed, ground lignocellulosic feedstock can have at least one major dimension (e.g., length or diameter) in the range from 0.5 inches to 5 inches, in the range from 0.75 inches to 3 inches, or even in the range from 1 inch to 2.5 inches. In an exemplary embodiment, a cube shaped discrete unit of compressed, ground lignocellulosic feedstock can have dimensions of about 1.25 inches×1.25 inches×1.25 inches.

The ground lignocellulosic feedstock can be compressed to form at least one discrete unit using a compressing system. For example, a compressing system can be configured to compress at least a portion of the ground lignocellulosic feedstock to form a plurality of discrete units having a bulk density as described herein (e.g., in the range from 4 pounds per cubic foot to 25 pounds per cubic foot).

In some embodiments, a compressing system includes an extruder device including one or more extruder dies. The extruder device can be configured to apply pressure to at least a portion of the ground lignocellulosic feedstock so that at least a portion of the ground feedstock passes through the one or more extruder dies to form at a plurality of discrete units having a bulk density in the range from 4 pounds per cubic foot 25 pounds per cubic foot. In some embodiments, the extruder device is a radial extruding device that is configured so that the ground lignocellulosic feedstock can pass through the radial extruding device to form a plurality of discrete units. Radial extruders can also be referred to as "cubers."

In some embodiments, a cutting device is not necessary to form the discrete units as the compressed, ground lignocellulosic feedstock exits an extruder die because the discrete units can passively break off due to their own weight. However, a cutting device may be used to provide relatively more consistent lengths of discrete units.

Factors that can influence the properties of a discrete unit of compressed, ground lignocellulosic feedstock include one or more of the configuration of an extruder die, the particle size of the ground lignocellulosic feedstock, the moisture content of the ground lignocellulosic feedstock, the type of the lignocellulosic feedstock, and the like. As mentioned above, in some embodiments, lignocellulosic feedstocks such as corn stover and those similar to corn stover can be particularly desirable because their natural form can be bent and interlocked with other like pieces of compressed ground lignocellulosic feedstock, thereby forming a discrete unit.

Configuration of an Extruder Die

The size of an extruder die opening can influence the degree to which the lignocellulosic feedstock is compressed, which can in turn influence the density and/or Pellet Durability Index of a plurality of discrete units that are formed. For example, for ground lignocellulosic feedstock of a given type and having a given particle size and moisture content, as the size of an extrusion die opening increases the compression that the ground lignocellulosic feedstock is subjected to can decrease which can decrease the bulk density and/or Pellet Durability Index of a plurality of discrete units that are formed.

The size of an extrusion die can be any desired size. In some embodiments, the size of an extrusion die (e.g., a radial extrusion die) exit opening having a square-shaped opening can be 0.5 inches or greater. In some embodiments, the size of an extrusion die (e.g., a radial extrusion die) exit opening having a square-shaped opening can be in the range from 0.5 inches to 5 inches, from 0.5 inches to 2 inches, or even from 0.75 inches to 2 inches.

In some embodiments, the size of an extrusion die (e.g., a radial extrusion die) entry opening having a square-shaped opening can be 1 inch or greater. In some embodiments, the size of an extrusion die (e.g., a radial extrusion die) exit opening having a square-shaped opening can be in the range from 0.5 inches to 1 inch, from inch to 1.5 inches, or even from 1.5 inches to 2 inches.

In some embodiments, the length (i.e., the distance between the die entrance and exit) of an extrusion die (e.g., a radial extrusion die) can be 6 inches or greater. In some embodiments, the length of an extrusion die (e.g., a radial extrusion die) can be in the range from 3 inches to 5 inches, from 4 inches to 6 inches, or even from 6 inches to 8 inches.

The cross section of the flow path of an extrusion die can be any desired shape. For example, it can be rectangular, square, circular, and the like.

Figure 4A:
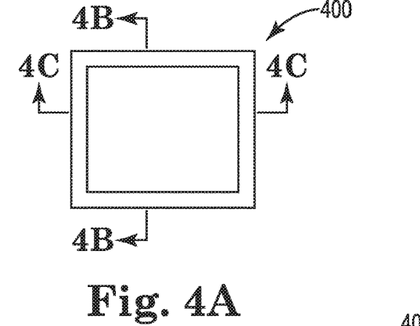
FIG. 4A shows a sketched, top view of an exemplary embodiment of a radial extrusion die.
Figure 4B:
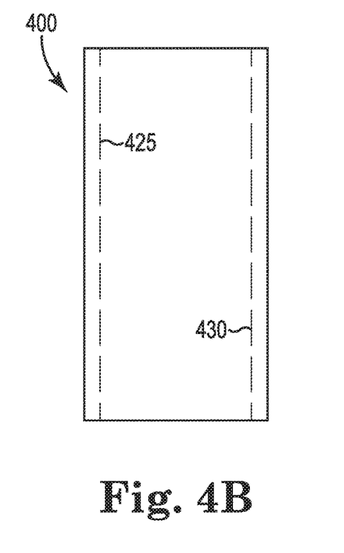
FIG. 4B shows a sketched, cross-sectional elevation view of the die in FIG. 4A.
Figure 4C:
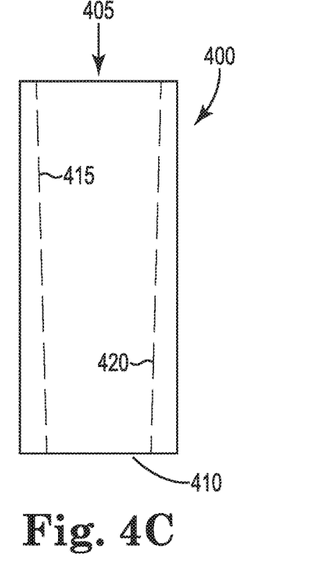
FIG. 4C shows a second, sketched, cross-sectional elevation view of the die in FIG. 4A.

In some embodiments, an extruder die can include a taper. The taper of an extruder die opening can influence the density and/or Pellet Durability Index of a plurality of discrete units that are formed. In some embodiments, an extrusion die (e.g., a radial extrusion die) can taper in a manner from where ground lignocellulosic feedstock enters the die to where it exits. That is, an extrusion die can taper from a relatively large opening size where ground lignocellulosic feedstock enters the die to a relatively small opening size where ground lignocellulosic feedstock exits the die. In some embodiments, a die opening having a square or rectangular cross-section can have a two-way taper or a four-way taper. A two-way taper refers to a die passage-way that has only two opposing sides that taper from where ground lignocellulosic feedstock enters the die to where it exits. A four-way taper refers to a die passage-way where all four sides taper from where ground lignocellulosic feedstock enters the die to where it exits. In some embodiments, an extrusion die can taper in a linear manner. FIGS. 4A-4C show an exemplary embodiment of a radial extrusion two-way taper die 400 that tapers in a linear manner. FIG. 4A shows a top view of die 400. FIG. 4B shows a cross-sectional elevation view of the front of die 400, where inner sides 425 and 430 are straight and do not taper from inlet 405 to outlet 410. FIG. 4C shows a cross-sectional elevation view of the side of die 400, where inner sides 415 and 420 are linear and taper from inlet 405 to outlet 410.

Figure 5:
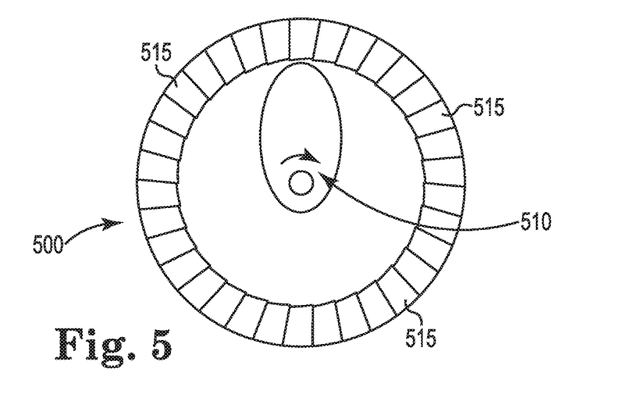
FIG. 5 shows a sketched view of an exemplary radial extruder.

FIG. 5 shows a sketched view of an exemplary radial extruder 500. Inner plate or roller 510 can rotate and push ground lignocellulosic feedstock out through radially formed dies 515 to form a plurality of discrete units.

Figure 6A:
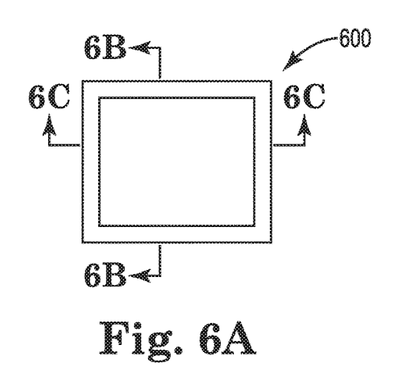
FIG. 6A shows a sketched, top view of an exemplary embodiment of a radial extrusion die.
Figure 6B:
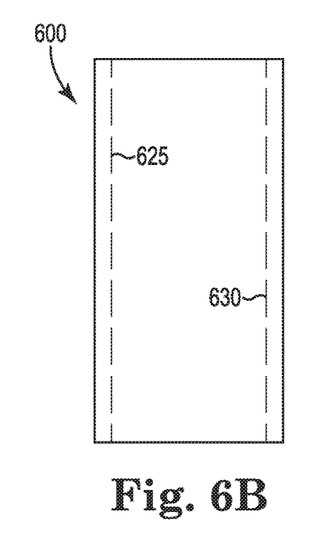
FIG. 6B shows a sketched, cross-sectional elevation view of the die in FIG. 6A.
Figure 6C:
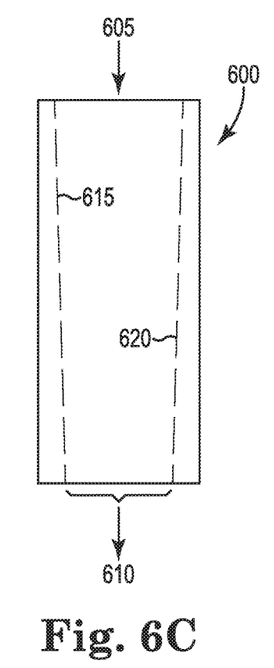
FIG. 6C shows a second, sketched cross-sectional elevation view of the die in FIG. 6A.
Figure 7:
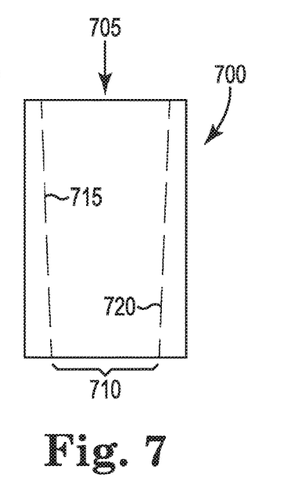
FIG. 7 shows a sketched cross-sectional elevation view of a shortened version of the die in FIG. 6C.

In some embodiments, an extruding die of an extruding device can be adjusted to provide a desired bulk density and/or Pellet Durability Index. For example, shortening an existing extruding die can reduce the residence time of the ground lignocellulosic feedstock as it passes through the die, which can reduce the bulk density as compared to a relatively longer extruder die that is otherwise identical to the shortened die. While not being bound by theory, it is believed that a reduced residence time can reduce the friction and compaction experienced by the ground lignocellulosic feedstock. In more detail, in some embodiments a radial extrusion die can taper (e.g., linearly in either a two-way or four-way manner) in a direction from where ground lignocellulosic feedstock enters the die to where it exits. That is, a radial extrusion die can taper from a relatively large opening size where ground lignocellulosic feedstock enters the die to a relatively small opening size where ground lignocellulosic feedstock exits the die. Such a die can be adjusted by shortening (i.e., removing) at least a portion of the die near the die exit end so as to increase the die exit opening size. FIGS. 6A-6C show an exemplary embodiment of a radial extrusion two-way taper die 600 that tapers in a linear manner. FIG. 6A shows a top view of die 600. FIG. 6B shows a cross-sectional elevation view of die 600, where inner sides 625 and 630 are straight and do not taper from inlet 605 to outlet 610. FIG. 6C shows a cross-sectional elevation view of die 600, where inner sides 615 and 620 are linear and taper from inlet 605 to outlet 610. FIG. 7 shows a side view of a die 700, which is a shortened version of the die 600 shown in FIG. 6C. As shown in FIG. 7, the die 700 represents die 600 being shortened by removing a portion of the die near die exit 610. Accordingly, the opening of die 700 near die exit 710 is larger than compared to the opening of die 600 near die exit 610. The die opening near die inlet 705 is the same size as the die opening in die 600 near die opening 605. Also, inner sides 715 and 720 are linear and taper from inlet 705 to outlet 710.

Particle Size of the Ground Lignocellulosic Feedstock

The particle size of the ground lignocellulosic feedstock can influence the degree to which the lignocellulosic feedstock can form an interlocking structure so as to form a discrete unit. For example, for a given extrusion die opening size and a given feedstock flowrate and type having a given moisture content, as the particle size of the lignocellulosic feedstock decreases the compression that the ground lignocellulosic feedstock is subjected to can decrease which may decrease the ability of the ground lignocellulosic feedstock from forming an interlocking structure so as to form a discrete unit.

In some embodiments, the size of the ground lignocellulosic feedstock is at least 0.5 times the size of an extruder die exit opening. In some embodiments, at least a portion of the ground lignocellulosic feedstock includes particles having a length and a width, and wherein the average length of said particles is 12 inches or less. In some embodiments, the average length of said particles is in the range from ¼ inches to 10 inches, in the range from ½ inches to 5 inches, or even in the range from ⅝ inches to 4 inches.

Moisture Content of the Ground Lignocellulosic Feedstock

The moisture content of the ground lignocellulosic feedstock can influence the hardness and/or bulk density of the plurality of discrete units. For example, for a given extrusion die opening size and a ground lignocellulosic feedstock of a given type and having a given particle size, as moisture content of the ground lignocellulosic feedstock decreases (becomes more dry) the hardness of the discrete unit tends to increase and vice versa. Also, as the moisture content of the ground lignocellulosic feedstock decreases (becomes more dry) the bulk density of the discrete units tends to increase and vice versa.

In some embodiments, at least a portion of the ground lignocellulosic feedstock has a moisture content in the range from 10 to 50 percent by total weight of the ground lignocellulosic feedstock. In other embodiments, at least a portion of the ground lignocellulosic feedstock has a moisture content in the range from 10 to 30 percent by total weight of the ground lignocellulosic feedstock. In other embodiments, at least a portion of the ground lignocellulosic feedstock has a moisture content in the range from 13 to 20 percent by total weight of the ground lignocellulosic feedstock. In still other embodiments, at least a portion of the ground lignocellulosic feedstock has a moisture content in the range from 14 to 19 percent by total weight of the ground lignocellulosic feedstock.

In some embodiments, the hardness of a discrete unit of ground lignocellulosic feedstock can be controlled by controlling the moisture content of the ground lignocellulosic feedstock. The moisture content of the ground lignocellulosic feedstock can be controlled by drying the lignocellulosic feedstock, wetting the lignocellulosic feedstock, and combinations thereof, prior to or while the ground lignocellulosic feedstock is compressed to form a discrete unit as described herein.

In some embodiments, the moisture content of the ground lignocellulosic feedstock can be controlled by keeping the extruder die size constant and contacting at least a portion of the lignocellulosic feedstock with an aqueous composition before grinding and/or after grinding and/or during compressing so that at least a portion of the ground lignocellulosic feedstock has a desired moisture content.

The lignocellulosic feedstock can be contacted with an aqueous composition using a wetting system. A wetting system can be coupled to the system for processing lignocellulosic feedstock and configured to apply an aqueous composition to at least a portion of the lignocellulosic feedstock with an aqueous composition before grinding and/or after grinding and/or during compressing so that at least a portion of the ground lignocellulosic feedstock has a desired moisture content.

An aqueous composition for wetting the lignocellulosic feedstock can include any aqueous composition that is compatible with a given process to generate a biochemical. The aqueous composition can be obtained from a recycle stream, a make-up stream, and combinations thereof. In exemplary embodiments, the aqueous composition can include water, one or more waste streams from a cellulosic ethanol process, one or more waste streams from a corn ethanol process, and combinations thereof. Exemplary waste streams from a cellulosic ethanol process include syrup, effluent from an anaerobic digester, lignin cake that is recovered after fermentation, and the like. Exemplary waste streams from a corn ethanol process include syrup, and the like.

An aqueous composition can be applied to the lignocellulosic feedstock in any desirable form. For example, the aqueous composition can be applied in steam form, liquid form, and combinations thereof.

Using a Discrete Unit of Compressed Lignocellulosic Feedstock

As described herein, a discrete unit of compressed lignocellulosic feedstock can have improved handling properties, especially in the context of downstream processes in a biorefinery to generate one or more biochemicals. For example, a plurality of discrete units of compressed lignocellulosic feedstock can be used in a biorefinery that makes one or more biochemicals such as ethanol by hydrolyzing polysaccharides in lignocellulosic feedstock into monosaccharides and converting the monosaccharides into the one or more biochemical via a microorganism such as yeast.

In some embodiments, at least one discrete unit can be contacted with an aqueous composition to hydrolyze at least a portion of the hemicellulose and/or cellulose and form a liquid component and a solid component. In some embodiments, at least a portion of the liquid component can be separated from the solid component. As described herein above, the discrete units of compressed, ground lignocellulosic feedstock (or a portion thereof) can advantageously have a reduced tendency to plug a screen used to separate liquid from a solid. Without being bound by theory, it is believed that the bent structure of the compressed, ground lignocellulosic feedstock helps prevent the lignocellulosic feedstock from lying flat on the screen and building up to an undue degree such that liquid can barely pass, if at all, through the screen. Instead, the bent structure can permit liquid to pass through the screen at a desired flow rate even though the bent lignocellulosic feedstock may build up on a side of the screen. Alternatively, the liquid component and solid component can be subsequently processed in one or more unit operations without separating the liquid component from the solid component.

In more detail with respect to hydrolyzing a discrete unit of lignocellulosic feedstock, hydrolyzing lignocellulosic feedstock can provide a solid component including glucan and lignin and a liquid component including a monosaccharide such as xylose and/or glucose. In some embodiments, the solid component can be separated from the liquid component so that the liquid component can be used for fermentation. The liquid component can be separated from the solid component after hydrolysis via one or more of screw presses, centrifuges, filter belts, filter presses, gravity screens, vibratory screens, and the like.

Hydrolysis of polysaccharides in lignocellulosic feedstock can occur by a wide variety of techniques such as contacting the lignocellulosic feedstock with hot water, acid, base, enzyme(s), and the like. Hydrolyzing lignocellulosic substrates to provide, e.g., xylose and/or glucose is described in, e.g., U.S. Pat. No. 5,424,417 (Torget et al.); U.S. Pat. No. 6,022,419 (Torget et al.); and U.S. Pat. No. 8,450,094 (Narendranath et al.), and U.S. Publication Number 2010/0233771 (McDonald et al.), wherein the entireties of said patent documents are incorporated herein by reference for all purposes.

Figure 2:
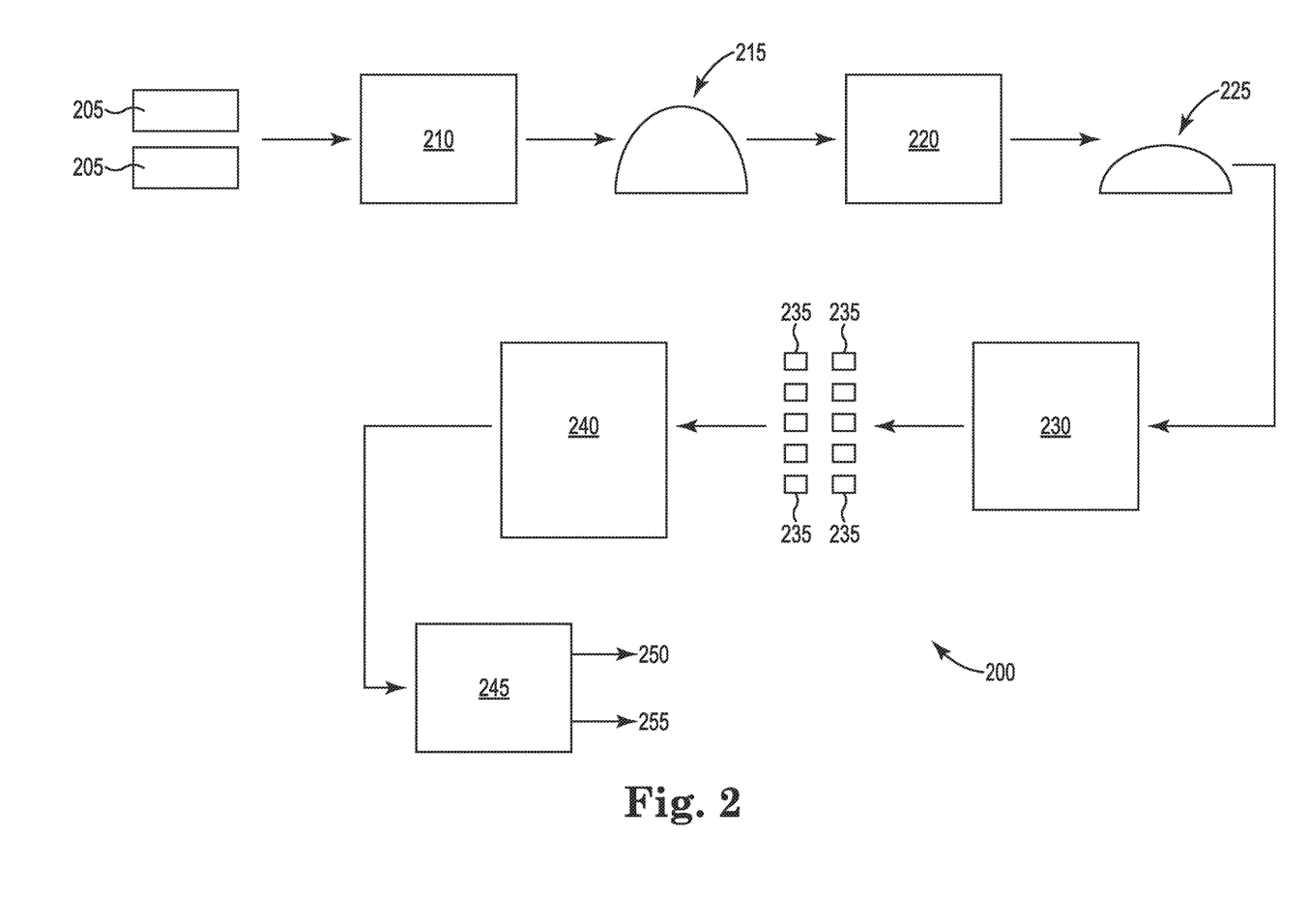
FIG. 2 shows an exemplary flow diagram illustrating an embodiment of a system according to the present disclosure.

FIG. 2 shows an exemplary flow diagram illustrating an embodiment of a system according to the present disclosure. System 200 for processing lignocellulosic feedstock includes a source of lignocellulosic feedstock 205. As shown, the source of lignocellulosic feedstock 205 includes a plurality of bales including the lignocellulosic feedstock such as corn stover. The bales 205 can be unbaled in unbaling system 210 to provide the unbaled lignocellulosic feedstock 215. The unbaled lignocellulosic feedstock 215 is in fluid communication with the grinding system 220.

The grinding system 220 is configured to grind the lignocellulosic feedstock 215 to provide ground lignocellulosic feedstock 225. The grinding system 220 is in fluid communication with a compressing system 230.

The compressing system 230 is configured to compress at least a portion of the ground lignocellulosic feedstock 225 to form a plurality of discrete units 235 having a bulk density in the range from 4 pounds per cubic foot to 25 pounds per cubic foot. In some embodiments, a compressing system 230 includes an extruder device (not shown) having one or more extruder dies. The extruder device can be configured to apply pressure to at least a portion of the ground lignocellulosic feedstock so that at least a portion of the ground feedstock passes through the one or more extruder dies to form a plurality of discrete units 235 having a bulk density in the range from 4 pounds per cubic foot 25 pounds per cubic foot.

As shown in FIG. 2, the system 200 also includes a hydrolyzing system 240 in fluid communication with the compressing system 230 and a source of the aqueous composition (not shown). The hydrolyzing system 240 is configured to contact the plurality of discrete units 235 with the aqueous composition to hydrolyze at least a portion of hemicellulose and/or cellulose in the lignocellulosic feedstock and form a liquid component and a solid component.

As shown in FIG. 2, system 200 also includes a separating system 245 in fluid communication with the hydrolyzing system 240 and configured to separate at least a portion of the liquid component 250 from the solid component 255. The separating system 245 includes at least one screen device (not shown) configured to retain the solid component 255 while at least a portion of the liquid component 250 passes through the screen device to separate at least a portion of the liquid component 250 from the solid component 255. Exemplary separating systems that include a screen device include centrifuges, filter belts, filter presses, gravity screens, vibratory screens, and the like. A screen device can include perforated sheets, wedgewires, etc. to help separate liquid from solid. Exemplary screen opening sizes are from 260 microns (0.010 inch) to 2540 microns (0.10 inch) depending on the material that is being dewatered.

Optionally, system 200 can include one or more wetting systems (not shown) coupled to the system 200 and configured to apply an aqueous composition to at least a portion of the lignocellulosic feedstock and/or the ground lignocellulosic feedstock so that the ground lignocellulosic feedstock has a desired moisture content (e.g., in the range from 10 to 50 percent by total weight of the ground lignocellulosic feedstock). For example, a wetting system could be coupled to system 200 in manner to apply an aqueous composition to the incoming bales 205, to the lignocellulosic feedstock in unbaling system 210, to the unbaled lignocellulosic feedstock 215, to the lignocellulosic feedstock in grinding system 220, to the ground lignocellulosic feedstock 225, and/or to the ground lignocellulosic feedstock in compressing system 230. The aqueous composition can be applied to the lignocellulosic feedstock and/or the ground lignocellulosic feedstock via any desired technique. Exemplary wetting techniques include dispensing, spraying, dipping, submerging, and the like. In one embodiment, the ground lignocellulosic feedstock 225 can be combined with an aqueous composition in a mixing auger (not shown) just before compressing system 230.

Optionally, system 200 can include a control system (not shown) operatively coupled to system 200 to control the bulk density of the plurality of discrete units. For example, as mentioned above, the moisture content of the ground lignocellulosic feedstock can be controlled, thereby controlling the bulk density of the plurality of discrete units. In one embodiment, the control system includes a controller configured to execute program instructions. The controller can be operatively coupled to a wetting system (not shown) and the compressing system 230 to cause the wetting system and the compressing system 230 to perform one or more of the program instructions. The program instructions can include measuring an ampere value of an electric extruder motor used to power an extruder device in compressing system 230. A plurality of ampere values can be correlated to moisture content values of the ground lignocellulosic feedstock that result in a desired bulk density of a plurality of discrete units that are formed. That is, the ampere values can indicate whether the ground lignocellulosic feedstock is too dry, too wet, or has an appropriate moisture content that results in a desired bulk density of the plurality of discrete units. If the ground lignocellulosic feedstock is too dry, then the wetting system can apply an appropriate amount of aqueous composition to bring the moisture content within specification. If the ground lignocellulosic feedstock has a moisture content within specification, then the controller can control the wetting system to not apply any aqueous composition at that time. In some embodiments, a target moisture content can be selected to control to so that the ground lignocellulosic feedstock is rarely, if at all, too wet and so that drying is not necessary. Accordingly, the program instructions can also include determining an amount of aqueous composition to apply to the ground lignocellulosic feedstock based on the ampere value to control the bulk density of the plurality of discrete units to be in the range from 4 pounds per cubic foot to 25 pounds per cubic foot.

Optionally, system 200 can include one or more cleaning systems to clean the lignocellulosic feedstock. FIG. 3 illustrates how a first cleaning system 305 and a second cleaning system can optionally be incorporated into system 200 in FIG. 2.

Figure 3:
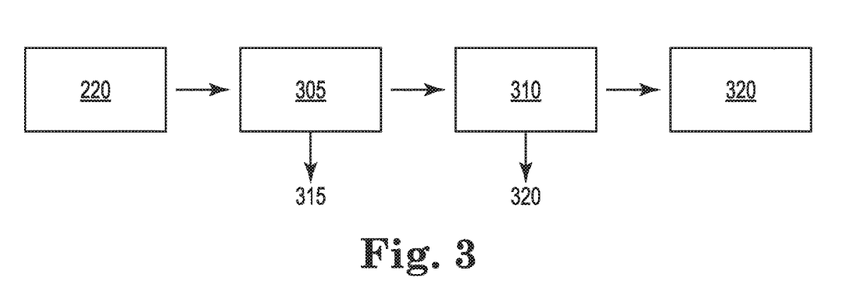
FIG. 3 shows an exemplary flow diagram illustrating an embodiment of a cleaning system according to the present disclosure.

As shown in FIG. 3, first cleaning system 305 is in fluid communication with the grinding system 220 to receive the ground lignocellulosic feedstock. The first cleaning system 305 can be configured to remove at least a portion of non-lignocellulosic feedstock material 315 from the ground lignocellulosic material. The non-lignocellulosic feedstock material 315 removed in the first cleaning system 305 can include dirt, silt, sand, and the like. Because dirt, silt, sand, and the like are relatively smaller particles, first cleaning system 305 can be referred to as a "fine separation" system. First cleaning system 305 can remove the non-lignocellulosic material 315 using a wide variety of separation techniques. Exemplary separation techniques for first cleaning system 305 include sifting lignocellulosic feedstock through a screen aperture; treating the lignocellulosic feedstock with an air or water current; density separation; combinations of these; and the like.

As also shown in FIG. 3, second cleaning system 310 is in fluid communication with the first cleaning system 305 to receive the ground lignocellulosic feedstock from first cleaning system 305. The second cleaning system 310 can be configured to remove at least a portion of non-lignocellulosic feedstock material 320 from the ground lignocellulosic material. The non-lignocellulosic feedstock material 320 removed in the second cleaning system 310 can include rock, tramp metal, glass, and the like. Because rock, tramp metal, glass, and the like are relatively larger particles, second cleaning system 310 can be referred to as a "coarse separation" system. Second cleaning system 310 can remove the non-lignocellulosic material 320 using a wide variety of separation techniques. Exemplary separation techniques for second cleaning system 320 include sifting lignocellulosic feedstock through a screen aperture; treating the lignocellulosic feedstock with an air or water current; magnet separation techniques; combinations of these; and the like.

The second cleaning system 310 is in fluid communication with the compressing system 230 so as to provide cleaned, ground lignocellulosic feedstock to compressing system 230.

It is noted that the order of first cleaning system 305 and second cleaning system 310 can be switched as desired. Further one or more additional first cleaning systems 305 and/or second cleaning systems 310 can be included as desired.

A system according to the present invention can include one or more optional systems to recover and/or concentrate one or more biochemicals. Exemplary optional systems include distillation systems and the like.

What is claimed is:

1. A method of processing lignocellulosic feedstock comprising:

grinding lignocellulosic feedstock to provide ground lignocellulosic feedstock pieces, wherein the ground lignocellulosic feedstock pieces each have a length and a width, and wherein the average length of said ground lignocellulosic feedstock pieces is in the range from 0.25 inches to 12 inches;

and compressing at least a portion of the ground lignocellulosic feedstock pieces to form a plurality of discrete units, wherein the plurality of discrete units have a bulk density in the range from 4 pounds per cubic foot to 25 pounds per cubic foot as measured by ASAE S269.4.

2. The method according to claim 1, wherein at least a portion of the ground lignocellulosic feedstock has a moisture content in the range from 10 to 50 percent by total weight of the ground lignocellulosic feedstock.

3. The method according to claim 1, further comprising contacting the lignocellulosic feedstock and/or the ground lignocellulosic feedstock with and aqueous composition so that at least a portion of the ground lignocellulosic feedstock has a moisture content in the range from 10 to 50 percent by total weight of the ground lignocellulosic feedstock.

4. The method according to claim 1, wherein the lignocellulosic feedstock comprises hemicellulose and cellulose and further comprising:

contacting the plurality of discrete units with an aqueous composition to hydrolyze at least a portion of the hemicellulose and/or cellulose and form a liquid component and a solid component.

5. The method according to claim 1, further comprising, before grinding, cleaning the ground lignocellulosic feedstock to remove at least a portion of non-lignocellulosic feedstock material from the ground lignocellulosic feedstock, wherein the non-lignocellulosic feedstock material is selected from the group consisting of dirt, silt, sand, rocks tramp metal, glass, and combinations thereof.

6. The method according to claim 1, wherein compressing comprises passing the lignocellulosic feedstock through one or more extruder dies to form the plurality of discrete units.

7. The method according to claim 6; wherein the one or more extruder dies each have an exit opening shape selected from the group consisting of a square-shaped opening, a rectangular-shaped opening, a circular-shaped opening, and combinations thereof; and wherein the average length of said ground lignocellulosic feedstock pieces is at least 0.5 times the largest dimension of the exit opening shape.

8. The method according to claim 1, wherein compressing comprises passing the lignocellulosic feedstock through a radial extruding device to form the plurality of discrete units.

9. The method according to claim 1, wherein the lignocellulosic feedstock comprises corn stover.

10. The method according to claim 1, further comprising, prior to grinding, unbaling a bale of lignocellulosic feedstock to provide the lignocellulosic feedstock for grinding.

11. The method according to claim 1, wherein the plurality of discrete units have a Pellet Durability Index of less than 90 as measured by ASAE 5269.4.

12. A system for processing lignocellulosic feedstock comprising:
a source of lignocellulosic feedstock;
a grinding system configured to grind the lignocellulosic feedstock to provide ground lignocellulosic feedstock pieces, wherein the ground lignocellulosic feedstock pieces each have a length and a width, and wherein the average length of said ground lignocellulosic feedstock pieces is in the range from 0.25 inches to 12 inches, and wherein the source of lignocellulosic feedstock is in fluid communication with the grinding system; and
a compressing system configured to compress at least a portion of the ground lignocellulosic feedstock pieces to form a plurality of discrete units, wherein the plurality of discrete units have a bulk density in the range from 4 pounds per cubic foot to 25 pounds per cubic foot as measured by ASAE S269.4, wherein the grinding system is in fluid communication with the compressing system.

13. The system according to claim 12, further comprising a wetting system coupled to the system for processing lignocellulosic feedstock and configured to apply an aqueous composition to at least a portion of the lignocellulosic feedstock and/or the ground lignocellulosic feedstock.

14. The system according to claim 13, wherein the wetting system is configured to apply an aqueous composition to at least a portion of the lignocellulosic feedstock and/or the ground lignocellulosic feedstock so that the ground lignocellulosic feedstock has a moisture content in the range from 10 to 50 percent by total weight of the ground lignocellulosic feedstock.

15. The system according to claim 12, wherein the lignocellulosic feedstock comprises hemicellulose and cellulose and further comprising:
a source of an aqueous composition;
a hydrolyzing system in fluid communication with the compressing system and the source of the aqueous composition, wherein the hydrolyzing system is configured to contact the plurality of discrete units with the aqueous composition to hydrolyze at least a portion of the hemicellulose and/or cellulose and form a liquid component and a solid component; and
optionally, a separating system in fluid communication with the hydrolyzing system and configured to separate at least a portion of the liquid component from the solid component, wherein the separating system comprises at least one screen device configured to retain the solid component while at least a portion of the liquid component passes through the screen device to separate at least a portion of the liquid component from the solid component.

16. The system according to claim 12, wherein the compressing system comprises an extruder device including one or more extruder dies, wherein the extruder device is configured to apply pressure to at least a portion of the ground lignocellulosic feedstock so that at least a portion of the ground feedstock passes through the one or more extruder dies to form the plurality of discrete units having a bulk density in the range from 4 pounds per cubic foot 25 pounds per cubic foot.

17. The system according to claim 12, further comprising:
a first cleaning system in fluid communication with the grinding system to receive the ground lignocellulosic feedstock, wherein the first cleaning system is configured to remove at least a portion of non-lignocellulosic feedstock material from the ground lignocellulosic material, wherein the non-lignocellulosic feedstock material is selected from the group consisting of dirt, silt, sand, and combinations thereof; and
a second cleaning system in fluid communication with the first cleaning system to receive the ground lignocellulosic feedstock, wherein the second cleaning system is configured to remove at least a portion of non-lignocellulosic feedstock material from the ground lignocellulosic material, wherein the non-lignocellulosic feedstock material is selected from the group consisting of rock, tramp metal, glass, and combinations thereof, wherein the grinding system is in fluid communication with the second cleaning system.

18. The system according to claim 12, wherein the lignocellulosic feedstock comprises corn stover.

19. The system according to claim 12, further comprising:
a source of a plurality of bales comprising the lignocellulosic feedstock; and
an unbaling system that can unbale the plurality of bales to provide the unbaled lignocellulosic feedstock to the grinding system.

20. A system for processing lignocellulosic feedstock comprising:
a source of lignocellulosic feedstock;
a grinding system configured to grind the lignocellulosic feedstock to provide ground lignocellulosic feedstock pieces;
a compressing system configured to compress at least a portion of the ground lignocellulosic feedstock pieces to form a plurality of discrete units, wherein the plurality of discrete units have a bulk density in the range from 4 pounds per cubic foot to 25 pounds per cubic foot as measured by ASAE S269.4, wherein the grinding system is in fluid communication with the compressing system;
a wetting system coupled to the system for processing lignocellulosic feedstock and configured to apply an aqueous composition to at least a portion of the lignocellulosic feedstock and/or the ground lignocellulosic feedstock pieces;
a control system operatively coupled to the system to control the bulk density of the plurality of discrete units to be in the range from 4 pounds per cubic foot to 25 pounds per cubic foot, wherein the compressing system comprises an extruder device having an electric extruder motor, wherein the control system comprises a controller configured to execute program instructions, wherein the controller is operatively coupled to the wetting system and the compressing system to cause the wetting system and the compressing system to perform one or more of the program instructions, and wherein the program instructions comprise:
  measuring an ampere value of the electric extruder motor;
  determining an amount of aqueous composition to apply to the ground lignocellulosic feedstock based on the ampere value to control the bulk density of the plurality of discrete units to be in the range from 4 pounds per cubic foot to 25 pounds per cubic foot.

* * * * *